(12) United States Patent
Koneru et al.

(10) Patent No.: US 11,510,893 B1
(45) Date of Patent: *Nov. 29, 2022

(54) METHOCARBAMOL COMPOSITION AND RELATED METHODS

(71) Applicant: Exela Sterile Medicines LLC, Lenoir, NC (US)

(72) Inventors: Phanesh B. Koneru, Ashburn, VA (US); John Maloney, Lenoir, NC (US)

(73) Assignee: Exela Sterile Medicines LLC, Lenoir, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/579,278

(22) Filed: Jan. 19, 2022

Related U.S. Application Data

(63) Continuation of application No. 16/953,010, filed on Nov. 19, 2020, now Pat. No. 11,266,621, which is a continuation-in-part of application No. 16/524,130, filed on Jul. 28, 2019, now abandoned, which is a continuation of application No. 14/874,233, filed on Oct. 2, 2015, now abandoned.

(60) Provisional application No. 62/058,763, filed on Oct. 2, 2014.

(51) Int. Cl.
*A61K 31/27* (2006.01)
*A61K 9/08* (2006.01)
*A61K 9/00* (2006.01)

(52) U.S. Cl.
CPC ............ *A61K 31/27* (2013.01); *A61K 9/0019* (2013.01); *A61K 9/08* (2013.01)

(58) Field of Classification Search
CPC ........................... A61K 31/085; A61K 9/0019
See application file for complete search history.

(56) References Cited

U.S. PATENT DOCUMENTS 11,266,621 B1 * 3/2022 Koneru ................ A61K 9/0019

* cited by examiner

*Primary Examiner* — Ernst V Arnold
(74) *Attorney, Agent, or Firm* — Polsinelli PC

(57) ABSTRACT

Stable methocarbamol ready to use compositions for parenteral administration including parenteral infusion are provided. In certain embodiments, the compositions are sterile, isotonic, and particulate-matter-free. Further, the compositions reduce or avoid allergic reactions to latex, reduce or avoid extravasation, and permit administration of methocarbamol to subjects having renal pathology. Methods of manufacture and methods of administration are also provided.

20 Claims, No Drawings

METHOCARBAMOL COMPOSITION AND RELATED METHODS

CROSS-REFERENCE TO RELATED APPLICATIONS

This application is a continuation of U.S. patent application Ser. No. 16/953,010, filed on Nov. 19, 2020, which is a continuation-in-part of U.S. patent application Ser. No. 16/524,130, filed on Jul. 28, 2019, which is a continuation of U.S. patent application Ser. No. 14/874,233, filed on Oct. 2, 2015, which claims the benefit of U.S. Provisional Patent Application Ser. No. 62/058,763 filed on Oct. 2, 2014, each of which is incorporated herein by reference.

FIELD OF THE INVENTION

The present invention involves methocarbamol compositions, dosages, systems, and related methods. Accordingly, the present invention involves the fields of pharmacy, medicine, and chemistry.

BACKGROUND

Methocarbamol is a muscle relaxant that has been in use for several years in the United States and other countries. Liquid methocarbamol for parenteral administration has been known. See for example, Robaxin sold by West-Ward Pharmaceuticals. According to the labeling approved by the US FDA, Robaxin (methocarbamol injection, USP), is a central nervous system (CNS) depressant with sedative and musculoskeletal relaxant properties. It is a sterile, pyrogen-free solution intended for intramuscular or intravenous administration.

Each mL of Robaxin contains: methocarbamol, USP 100 mg, polyethylene glycol 300, NF 0.5 mL, Water for Injection, USP q.s. The pH is adjusted, when necessary, with hydrochloric acid and/or sodium hydroxide. The chemical name of methocarbamol is 3-(2-methoxyphenoxy)-1,2-propanediol 1-carbamate and has the empirical formula of $C_{11}H_{15}NO_5$. Its molecular weight is 241.24. The structural formula is shown below:

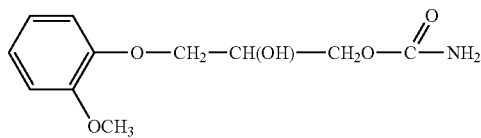

Methocarbamol with 50% PEG 300 vehicle was studied for potential hemolytic effects. See Scott, R B, et al, Clin. Pharmacol. Ther. 1977, 21(2): 208-211. The authors concluded that: "Hemolysis, though detectable, did not exceed levels found under physiologic circumstances such as exercise, and represents only a small fraction of the normal daily hemolysis of aged erythrocytes." See Abstract.

With respect to renal patients, a study was conducted on the pharmacokinetics of methocarbamol in renal dialysis patients. See, Sica, D A, et al, Eur J Clin Pharmacol 1990 39(2): 193-4. The study concluded that: "These results indicate no significant differences with respect to methocarbamol absorption, with the relative systemic availability in patients being 113%. These data suggest that absorption and elimination of methocarbamol is similar between normal subjects and patients undergoing maintenance haemodialysis."

However, while methocarbamol injection has been used for many years, the labeling indicates that the product is contraindicated in certain patients due to the presence of polyethylene glycol 300 in its formulation. The following is an excerpt from the approved labeling of the ROBAXIN product:

Contraindications

ROBAXIN Injectable should not be administered to patients with known or suspected renal pathology. This caution is necessary because of the presence of polyethylene glycol 300 in the vehicle. A much larger amount of polyethylene glycol 300 than is present in recommended doses of ROBAXIN Injectable is known to have increased pre-existing acidosis and urea retention in patients with renal impairment. Although the amount present in this preparation is well within the limits of safety, caution dictates this contraindication.

Despite the fact that methocarbamol has been shown to be safe and beneficial as an active agent, the other ingredients contained in the approved formulation undermine these benefits with the negative side effects they cause. A number of other issues also hinder the presently approved methocarbamol product as mentioned further herein.

SUMMARY OF THE INVENTION

In light of this conflicting state of literature as to the safety of methocarbamol intravenous compositions, certain invention embodiments include formulations of methocarbamol that have less than 56 wt % of polyethylene glycol (PEG). In one aspect, the compositions comprise, consist of, or consist essentially of methocarbamol in an amount of from about 1 mg/ml to about 10 mg/ml, a tonicity agent, and water. In an additional aspect, the compositions can further contain a pH adjuster and a buffer. In still an additional aspect, the composition is isotonic. In certain examples, the compositions are PEG-free or substantially PEG-free.

In another embodiment, an injectable dosage form, or dose is described. The injectable dosage form can comprise, consist of, or consist essentially of methocarbamol in an amount from 1 mg/ml to 20 mg/ml, a tonicity agent, water, and less than 56 wt % PEG. In an additional aspect, the injectable dosage form further contains a pH adjuster and/or a buffer. Further, the injectable dosage form is isotonic. In certain examples, the injectable dosage form is PEG-free or substantially PEG-free.

Other invention embodiments include systems for administration of an injectable methocarbamol composition, dose, or dosage form. The system can comprise, consist of, or consist essentially of a container and a methocarbamol composition. In one aspect, the container can hold a volume of the composition, dose, or dosage form, of from about 50 ml to about 1000 ml, or from about 100 mL to about 500 mL. In another aspect, the composition can comprise, consist of, or consist essentially of methocarbamol in a solution in an amount from 1 mg/ml to 20 mg/ml, a tonicity agent, water, and less than 50 v/v % PEG. In an additional aspect, the composition can further contain a pH adjuster and a buffer. Further, the composition is isotonic. In certain examples, the composition is PEG-free or substantially PEG-free.

Yet additional invention embodiments include methods for preventing an adverse health effect associated with administration of an injectable methocarbamol composition, dose, or dosage form to a subject. In one aspect, such a method can comprise, consist of, or consist essentially of infusing a pre-mixed, injectable methocarbamol solution from a container of a therapeutically effective amount to the subject. In one aspect, the methocarbamol solution can comprise, consist of, or consist essentially of methocarbamol in an amount from about 1 mg/ml to about 20 mg/ml, a tonicity agent, water, and less than 0.56 mg/ml PEG. In an additional aspect, the solution further contains a buffer. Further, the composition is isotonic. In certain examples, the composition is PEG-free or substantially PEG-free.

Still further invention embodiments include processes for preparing a solution of methocarbamol, the process comprising: acidifying water to a pH of about 3 to about 5, wherein the acidifying comprises adding a pH adjusting agent to the water; and contacting the acidified water with methocarbamol to form a solution of methocarbamol, wherein the solution has about 1.0% w/w or less of 1-hydroxy-3-(2-methoxyphenoxy)propan-2-yl carbamate as measured by common analytical techniques such as High Pressure Liquid Chromatography (HPLC) or Ultra Pressure Liquid Chromatography (UPLC), or the like. In one aspect, the process further comprises adding a tonicity agent and/or a buffer to the water before the addition of the acidifying agent and pH adjustment to about 3 to about 5. In another aspect, the process further comprises filter sterilizing the methocarbamol solution, and then aseptically filling a container with the sterilized solution and sealing. In an additional aspect, the methocarbamol solution is PEG free or substantially PEG free. In various embodiments, the methocarbamol solution may contain about 1 mg/mL to about 10 mg/mL methocarbamol, about 1 mg/mL to about 9 mg/mL methocarbamol, about 1 mg/mL to about 8 mg/mL methocarbamol, about 1 mg/mL to about 7 mg/mL methocarbamol, about 1 mg/mL to about 6 mg/mL methocarbamol, or about 1 mg/mL to about 5 mg/mL methocarbamol.

DETAILED DESCRIPTION

Before the present invention is disclosed and described, it is to be understood that this invention is not limited to the particular structures, process steps, or materials disclosed herein, but is extended to equivalents thereof as would be recognized by those ordinarily skilled in the relevant arts. It should also be understood that terminology employed herein is used for the purpose of describing particular embodiments only and is not intended to be limiting.

In describing and claiming the present invention, the following terminology will be used in accordance with the definitions set forth below.

As used herein, "methocarbamol" refers to a synthetic molecule described above. Unless specified otherwise, the term is understood to refer to racemic mixtures, as well as enantiomeric forms (for example its R-enantiomer), and any of their various pharmaceutically acceptable salts. For example, an R-methocarbamol can be prepared and used in the present invention instead of the racemic mixture. When an R-enantiomer is used, the compositions, doses, or dosage forms of the present invention can comprise the R-enantiomer of methocarbamol in an amount of from about 1 mg/ml to about 50 mg/ml; or 25 mg/ml; or 15 mg/ml; or 10 mg/ml; or 5 mg/ml; or 3 mg/ml; or 2 mg/ml.

As used herein, "subject" refers to a mammal. Examples of subjects include humans, and may also include other animals such as horses, pigs, cattle, dogs, cats, rabbits, and aquatic mammals. In one aspect, the subject can be a human. In another aspect, the subject can be a human with an existing renal pathology.

As used herein, the term "particulate-matter-free" or its grammatical equivalents, such as "particulate free," or "particle free" refer to a state in which the composition of the present invention meets the USP requirements for particulate matter in parenteral solutions. See for example, USP XXXII, Chapter 788. One of skill in the art understands and knows how to assess whether a given composition meets USP particulate matter requirements.

Concentrations, amounts, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 2 to about 50" should be interpreted to include not only the explicitly recited values of 2 to 50, but also include all individual values and sub-ranges within the indicated range. Thus, included in this numerical range are individual values such as 2, 2.4, 3, 3.7, 4, 5.5, 10, 10.1, 14, 15, 15.98, 20, 20.13, 23, 25.06, 30, 35.1, 38.0, 40, 44, 44.6 45, 48 and sub-ranges such as from 1-3, from 2-4, from 5-10, from 5-20, from 5-25, from 5-30, from 5-35, from 5-40, from 5-50, from 2-10, from 2-20, from 2-30, from 2-40, from 2-50, from 10-15, from 10-20, from 10-30, from 10-40, from 10-50, from 20-30, from 20-25, from 20-40, from 20-50, etc. This same principle applies to ranges reciting only one numerical value as a minimum or a maximum. Furthermore, such an interpretation should apply regardless of the breadth of the range or the characteristics being described.

As used herein, the term "substantially" refers to the complete or nearly complete extent or degree of an action, characteristic, property, state, structure, item, or result. As an arbitrary example, when a composition is referred to as being "substantially" homogenous, it is to be understood that the composition is either completely homogenous or is nearly completely homogenous. The exact allowable degree of deviation from absolute completeness may in some cases depend on the specific context. However, generally speaking the nearness of completion will be so as to have the same overall result as if an absolute and total completion were obtained.

The use of "substantially" is equally applicable when used in a negative connotation to refer to the complete or near complete lack of an action, characteristic, property, state, structure, item, or result. As an arbitrary example, a composition that is "substantially free of" a material would either completely lack material, or so nearly completely lack the material that the effect would be the same as if it completely lacked the material. In other words, a composition that is "substantially free of" the material may still actually contain some such material so long as there is no measurable effect as a result thereof.

As used herein, the term "about" is used to provide flexibility to a numerical range endpoint by providing that a given value may be "a little above" or "a little below" the endpoint. For example, the endpoint may be within 10%, 8%, 5%, 3%, 2%, or 1% of the listed value. Further, for the sake of convenience and brevity, a numerical range of "about 50 mg/ml to about 80 mg/ml" should also be understood to provide support for the range of "50 mg/ml to 80 mg/ml."

In this disclosure, "comprises," "comprising," "containing" and "having" and the like can have the meaning ascribed to them in U.S. Patent law and can mean "includes," "including," and the like, and are generally interpreted to be open ended terms. The terms "consisting of" or "consists of" are closed terms, and include only the components, structures, steps, or the like specifically listed in conjunction with such terms, as well as that which is in accordance with U.S. Patent law. "Consisting essentially of" or "consists essentially of" have the meaning generally ascribed to them by U.S. Patent law. In particular, such terms are generally closed terms, with the exception of allowing inclusion of additional items, materials, components, steps, or elements, that do not materially affect the basic and novel characteristics or function of the item(s) used in connection therewith. For example, trace elements present in a composition, but not affecting the compositions nature or characteristics would be permissible if present under the "consisting essentially of" language, even though not expressly recited in a list of items following such terminology. In this specification when using an open ended term, like "comprising" or "including," it is understood that direct support should be afforded also to "consisting essentially of" language as well as "consisting of" language as if stated explicitly and vice versa.

An initial overview of technology embodiments is provided below and specific technology embodiments are then described in further detail. This initial summary is intended to aid readers in understanding the technology more quickly, but is not intended to identify key or essential features of the technology, nor is it intended to limit the scope of the claimed subject matter.

In one embodiment, the compositions of the current technology can include methocarbamol, a tonicity agent, water, and less than 56 wt % polyethylene glycol (PEG). In another embodiment, the composition can be used as an injectable dosage form.

In one invention embodiment, a methocarbamol composition, dose, or dosage form that is ready to administer to the patient is provided. In one aspect, a ready-to-use or ready-to-administer methocarbamol composition, dose or dosage form is a pre-mixed composition that can be administered as is, such as a composition that can be administered without further dilution at the point of use.

In another embodiment the methocarbamol composition or dosage form is injected or intravenously infused at a concentration of from about 1 mg/ml to about 10 mg/ml. In another embodiment, the infusion may be administered at a rate of from about 20 mg/minute to about 100 mg/minute. For example, a 200 mL premixed composition of methocarbamol at a concentration of 5 mg/mL may be infused at a rate that ranges from about 20 mg/minute (about 4 mL/minute) to about 50 mg/minute (about 10 mL/minute), or to about 70 mg/minute (about 14 mL/minute), or to about 100 mg/minute (about 20 mL/minute). The infusion may be completed in from about 10 minutes to about 20 minutes, or from about 10 minutes to about 30 minutes, or from about 10 minutes to about 50 minutes, or from about 10 minutes to about 60 minutes. In some cases, as desired by the physician, the infusion can be a slow drip such that the infusion may last 2 or 3 or 6 hours. In one aspect, the methocarbamol is present at a concentration of from about 1 mg/ml to about 10 mg/ml. In one aspect, the methocarbamol is present at a concentration of from about 5 mg/ml.

The ready-to-administer, injectable methocarbamol composition, dose, or dosage form is a sterile composition. Any suitable sterilization method that does not degrade the composition to below acceptable limits as discussed below can be used to achieve a sterile composition. For example, terminal sterilization can be accomplished in a suitable sterilizer employing steam, supersaturated water, or a combination thereof (generally known as heat sterilization). The appropriate sterilization conditions can be determined based on the number of units or containers and the size of the units or containers to be sterilized. In one aspect, sterilization is conducted in an air over-pressure type sterilizer or steam sterilizer or water cascade type sterilizer, each of which are commercially available. Exemplary time and temperature levels required for adequate sterilization can be achieved by maintaining a temperature of about 121 degrees C. for from about 7-8 minutes to about 30 minutes or more, as needed.

A preferred sterilization method is an aseptic method. Such aseptic sterilization may include filtration or radiation methods, which are well-known in the art. Accordingly, the present ready-to-use methocarbamol injectable composition or dosage form could be terminally sterilized or aseptically sterilized, and commercially produced in large quantities for commercial distribution.

As noted above, while methocarbamol has been in use for many years, its usage is restricted to a renally non-pathologic patient population. The approved labeling for Robaxin states that the product is contraindicated in patients that are known to or suspected of having renal pathology. Because a wide variety of disease conditions can affect or induce renal pathology, this is a significant limitation on the use of methocarbamol in a patient needing a parenteral dosage. In addition, a number of pharmaceutically active agents can also affect renal physiology/pathology, thereby exacerbating the need to observe the contraindication scrupulously in a hospital setting where polypharmacy is very common. This in turn creates an extra burden on the caregivers (physicians, pharmacists, nurses and other paramedical personnel) to ensure that methocarbamol is used with care.

However, preparation of a composition that is free of or substantially free of PEG-300, or other forms of PEG, is not straight forward because methocarbamol is not freely soluble in water. PEG-300 is an excellent solubilizer for methocarbamol, and removal thereof can cause methocarbamol to precipitate in an aqueous solution. Therefore, methocarbamol at the 100 mg/ml concentration, or even at lower concentrations, may require the aid of some polyethylene glycol or an alternative solubilizing agent.

Thus, the present inventors recognize that it would be highly advantageous to prepare an injectable methocarbamol composition with as little polyethylene glycol as possible. In one aspect, the polyethylene glycol of the current technology can be any PEG, such as from PEG-200 to PEG-400 (i.e. any PEG having an average molecular weight of from about 200 g/mol to about 400 g/mol), or combinations thereof. In one aspect, the PEG can be PEG-400. In one aspect, the PEG can be PEG-300. In one aspect, the PEG can be PEG-200.

In one aspect, the PEG can be present in the methocarbamol parenteral composition in an amount of less than 56 wt %. Included in the range of less than 56 wt % are all subranges of weight percentages less than 56 wt % in increments of 1 wt %, or a fraction thereof, such as less than 55 wt %, 50 wt %, 40 wt %, etc. For the purpose of clarity, any range of less than a specified wt % can also include 0 wt %.

Thus, in one aspect, the methocarbamol parenteral composition is substantially free of PEG. In another aspect, the methocarbamol parenteral composition is free of PEG.

Accordingly, it has been surprisingly discovered that not only physical attributes such as solubility but also clinical aspects such as extravasation and renal pathology concerns that give rise to patient contraindication issues can be solved by providing a ready-to-use methocarbamol composition in an aqueous vehicle with an amount of PEG less than 56 wt %, less than 56 w/v %, or less than 50 v/v % or the methocarbamol compositions that are free or substantially free of PEG, such as PEG-300 or any other form or PEG. Accordingly, the composition can be predominately water and administered via intravenous infusion at a concentration ranging from 1 mg/ml to 10 mg/ml or other suitable subrange such as 1 mg/ml to 7 mg/ml, 2 mg/ml to 6 mg/ml, 3 mg/ml to 6 mg/ml, or 4 mg/ml to 5 mg/ml. This product can be safely administered to patients/subjects that are in need of methocarbamol without being contraindicated due to their renal pathology, or be concerned about extravasation because the product is isotonic. Further, because the composition is a ready-to-use composition, no additional dilution (which requires aseptic techniques and thereby poses risks of contamination, and dilution errors) is needed prior to administration.

The aqueous solutions of methocarbamol when used at concentrations of about 2 mg/ml to about 10 mg/ml or in other subranges noted previously in water for injection as the predominant vehicle are stable for extended shelf-storage, are free or substantially free of particulate matter, are isotonic, and can be filter sterilized and/or terminally sterilized and thus be provided in a ready-to-administer presentation for ease of use in a clinical setting without needing to have a PEG as a solubilizer. The present invention therefore provides a methocarbamol ready-to-administer injectable formulation that has not been available up to now.

A stable solution or composition can be determined in a variety of manners, including assessment of physical appearance (e.g., visible particulate matter, color, etc.), as well as assay of the active ingredient (i.e., methocarbamol), degradation products of the active ingredient or other impurities, pH, impurities, and/or sub-visible particulate matter. Suitable methods for assessing these parameters are described in the USP.

In one aspect, a stable solution or composition can retain either at least 95 w/v % (e.g., 95 w/v %, 96 w/v %, 97 w/v %, 98 w/v %, 99 w/v %, or more) or from about 95 w/v % to about 105 w/v % of the initial concentration of methocarbamol under accelerated storage testing conditions. Accelerated storage testing conditions can be performed at 60 degrees C. for one week. Accordingly, in one example, a stable solution or composition can be a solution or composition that can retain at least 95 w/v % of the original amount of methocarbamol (i.e. unprecipitated and undegraded) after having been stored at 60 degrees C. for one week.

In another aspect, a stable solution or composition can retain either at least 95 w/v % (e.g., 95 w/v %, 96 w/v %, 97 w/v %, 98 w/v %, 99 w/v %, or more) or from about 95 w/v % to about 105 w/v % of the initial concentration of methocarbamol under ambient storage testing conditions. As is known in the art, ambient storage testing conditions are 25° C. and 60% relative humidity. For example, a stable solution or composition can be a solution or composition where at least 95 w/v % methocarbamol can remain unprecipitated and undegraded after storage at ambient temperature for at least 3 months. In one aspect, a stable solution or composition can be a solution or composition where at least 95 w/v % methocarbamol can remain unprecipitated and undegraded after storage at ambient temperature for at least 6 months. In one aspect, a stable solution or composition can be a solution or composition where at least 95 w/v % methocarbamol can remain unprecipitated and undegraded after storage at ambient temperature for at least 1 year. In one aspect, a stable solution or composition can be a solution or composition where at least 95 w/v % methocarbamol can remain unprecipitated and undegraded after storage at ambient temperature for about 3 to about 6 months. In one aspect, a stable solution or composition can be a solution or composition where at least 95 w/v % methocarbamol can remain unprecipitated and undegraded after storage at ambient temperature for about 6 months to about 1 year.

It is to be understood that the term unprecipitated means a solution of methocarbamol as described herein that complies with USP standard for particulate matter. Similarly, the term undegraded means a solution of methocarbamol as described herein that complies with generally ICH limits for impurities and degradation products as are known in the pharmaceutical arts. In certain cases the regulatory agency may allow impurities and degradation products to exceed the ICH limits with proper justification. Methocarbamol ready-to-use compositions described herein that comply with ICH limits or those that exceed the ICH limits but are justified and acceptable to the regulatory agencies are within the scope of the current disclosure and claims presented herein.

In another aspect, a stable solution or composition comprises about 1.0% w/w or less (e.g., about 0%, 0.1%, 0.2%, 0.3%, 0.4%, 0.5%, 0.6%, 0.7%, 0.8%, 0.9% w/w) of the impurity 1-hydroxy-3-(2-methoxyphenoxy)propan-2-yl carbamate after storage at ambient temperature for at least 1 month (e.g., about 1, 2, 3, 4, 5, 6, 7, 8, 9, 10, 11, 12, 13, 14, 15, 16, 17, 18, 19, 20, 21, 22, 23, 24 months or more). 1-Hydroxy-3-(2-methoxyphenoxy)propan-2-yl carbamate, also referred to herein as "the β-isomer") is a degradation product of methocarbamol. Applicants discovered that the generation of the β-isomer was particularly problematic and unexpected in compositions/solutions that are PEG free or substantially free of PEG. Controlling the pH of compositions and solutions to about pH 5 or less, controlling the pH during compounding to below pH 5.9, and controlling the order of addition of the components during compounding, individually and in combination, reduced formation of the β-isomer. In one example, a stable solution or composition can be a solution or composition containing no more than 1.0% w/w/ of the β-isomer after storage at ambient temperature for at least 3 months, at least 6 months, at least 12 months, at least 18 months, or at least 24 months. In one example, a stable solution or composition can be a solution or composition containing no more than 1.0% w/w of the β-isomer after storage at ambient temperature for about 3 months to about 6 months, about 6 months to about 12 months, or about 12 to about 24 months. In one example, a stable solution or composition can be a solution or composition containing about 0.5% w/w or less of the β-isomer after storage at ambient temperature for at least 3 months, at least 6 months, at least 12 months, at least 18 months, or at least 24 months. In one example, a stable solution or composition can be a solution or composition containing about 0.5% w/w or less of the β-isomer after storage at ambient temperature for about 3 months to about 6 months, about 6 months to about 12 months, or about 12 to about 24 months. In one example, a stable solution or composition can be a solution or composition containing about 0.3% w/w or less of the β-isomer after storage at ambient temperature for at least 3 months, at least 6 months, at least 12 months, at least 18 months, or at least 24 months. In one example, a stable solution or composition can be a solution or composition containing about 0.3% w/w or less of the β-isomer after storage at ambient temperature for about 3 months to about 6 months, or about 6 months to about 12 months.

In another aspect, a stable solution or composition comprises about 2.0% w/w or less (e.g., about 0%, 0.1%, 0.2%, 0.3%, 0.4%, 0.5%, 0.6%, 0.7%, 0.8%, 0.9%, 1.1%, 1.2%, 1.3%, 1.4%, 1.5%, 1.6%, 1.7%, 1.8%, 1.9% w/w) of the impurity guaifenesin after storage at ambient temperature for at least 1 month (e.g., about 1, 2, 3, 4, 5, 6, 7, 8, 9, 10, 11, 12, 13, 14, 15, 16, 17, 18, 19, 20, 21, 22, 23, 24 months or more). Guaifenesin is another degradation product of methocarbamol. In one example, a stable solution or composition can be a solution or composition containing no more than 2.0% w/w, or no more than 1.0% w/w of guaifenesin after storage at ambient temperature for at least 3 months, at least 6 months, at least 12 months, at least 18 months, or at least 24 months. In one example, a stable solution or composition can be a solution or composition containing no more than 1.0% w/w of guaifenesin after storage at ambient temperature for about 3 months to about 6 months, about 6 months to about 12 months, or about 12 to about 24 months. In one example, a stable solution or composition can be a solution or composition containing about 0.5% w/w or less of guaifenesin after storage at ambient temperature for at least 3 months, at least 6 months, at least 12 months, at least 18 months, or at least 24 months. In one example, a stable solution or composition can be a solution or composition containing about 0.5% w/w or less of guaifenesin after storage at ambient temperature for about 3 months to about 6 months, about 6 months to about 12 months, or about 12 to about 24 months. In one example, a stable solution or composition can be a solution or composition containing about 0.3% w/w or less of guaifenesin after storage at ambient temperature for at least 3 months, at least 6 months, at least 12 months, at least 18 months, or at least 24 months. In one example, a stable solution or composition can be a solution or composition containing about 0.3% w/w or less of guaifenesin after storage at ambient temperature for about 3 months to about 6 months, or about 6 months to about 12 months.

In another aspect, a stable solution or composition comprises about 3.0% w/w or less (e.g., about 0%, 0.1%, 0.2%, 0.3%, 0.4%, 0.5%, 0.6%, 0.7%, 0.8%, 0.9%, 1.1%, 1.2%, 1.3%, 1.4%, 1.5%, 1.6%, 1.7%, 1.8%, 1.9%, 2.1%, 2.2%, 2.3%, 2.4%, 2.5%, 2.6%, 2.7%, 2.8%, 2.9% w/w) of total impurities (inclusive of the β-isomer, guaifenesin and other impurities as measured by common analytical techniques such as HPLC, UPLC, and the like), after storage at ambient temperature for at least 1 month (e.g., about 1, 2, 3, 4, 5, 6, 7, 8, 9, 10, 11, 12, 13, 14, 15, 16, 17, 18, 19, 20, 21, 22, 23, 24 months or more). In one example, a stable solution or composition can be a solution or composition containing no more than 3.0% w/w, or no more than 2.0% w/w of total impurities after storage at ambient temperature for at least 3 months, at least 6 months, at least 12 months, at least 18 months, or at least 24 months. In one example, a stable solution or composition can be a solution or composition containing no more than 3.0% w/w, or no more than 2.0% w/w of total impurities after storage at ambient temperature for about 3 months to about 6 months, about 6 months to about 12 months, or about 12 to about 24 months. In one example, a stable solution or composition can be a solution or composition containing about 1.0% w/w or less of total impurities after storage at ambient temperature for at least 3 months, at least 6 months, at least 12 months, at least 18 months, or at least 24 months. In one example, a stable solution or composition can be a solution or composition containing about 1.0% w/w or less of total impurities after storage at ambient temperature for about 3 months to about 6 months, about 6 months to about 12 months, or about 12 to about 24 months. In one example, a stable solution or composition can be a solution or composition containing about 0.8% w/w or less of total impurities after storage at ambient temperature for at least 3 months, at least 6 months, at least 12 months, at least 18 months, or at least 24 months. In one example, a stable solution or composition can be a solution or composition containing about 0.8% w/w or less of total impurities after storage at ambient temperature for about 3 months to about 6 months, or about 6 months to about 12 months.

In one exemplary embodiment, a stable solution or composition of the present disclosure is PEG free, or substantially PEG free, and contains about 95 w/v % to about 105 w/v % of the initial concentration of methocarbamol and about 0.5% w/w or less of the β-isomer after storage at 25° C. and 60% RH for at least 3 months. In another exemplary embodiment, a stable solution or composition of the present disclosure is PEG free, or substantially PEG free, and contains about 98 w/v % to about 102 w/v % of the initial concentration of methocarbamol and about 0.5% w/w or less of the β-isomer after storage at 25° C. and 60% RH for at least 3 months.

It is understood that, in the pharmaceutical arts, levels of impurities and degradation products are expressed as % w/w wherein the numerator is the amount of the impurity or the degradation product and the denominator is the amount of the active drug, which in this case is methocarbamol.

In addition to the renal pathology contraindication due to the presence of PEG-300 in the currently marketed Robaxin injection (and its generic copies), the product may also cause hypersensitivity reactions in patients that are sensitive to latex because the product is supplied in a vial having a dry natural rubber stopper. See the following excerpt from the approved labeling for Robaxin:

Use in Patients with Hypersensitivity to Latex

The vial stopper contains dry natural rubber that may cause hypersensitivity reactions when handled by or when the product is injected in persons with known or possible latex sensitivity.

The present invention provides compositions in containers that are free of material consisting of dry natural rubber to avoid latex sensitivity. Any suitable container can be used that can prevent latex sensitivity in subjects/patients receiving the composition. For example, such containers can be made of a material that comprises glass or plastic. Additionally, containers, such as vials and syringes, can be capped with materials that are not made of dry natural rubber. In one aspect, such containers can comprise plastic flexible containers that are made of a material comprising polyethylene or polypropylene or a mixture thereof, or with a suitable inert material that does not cause undue adsorption/absorption issues or produce unacceptable leachable extractable foreign/toxic compounds.

Accordingly, the ready-to-use compositions of the present invention may be supplied in a glass vial (for example, Type II) or in a plastic container made from a material such as polyethylene, polypropylene or a combination thereof. The container may have any suitable size. For example, the container can range in size from about 50 ml to about 1000 ml or more if needed. In another aspect, the container size may range from about 50 ml to 500 ml. In some specific aspects, the container has a volume of about 50 ml, 100 ml, 200 ml, 250 ml, or 500 ml.

Another issue identified in the approved labeling of Robaxin injection is extravasation due to its hypertonicity, apparently caused by the presence of PEG-300. Extravasation results in severe pain to the patient and also leads to additional complications, sometimes requiring emergency procedures to remove the extravascular fluids. The approved labeling states:

Precautions

General

As with other agents administered either intravenously or intramuscularly, careful supervision of dose and rate of injection should be observed. Rate of injection should not exceed 3 mL per minute—i.e., one 10 mL vial in approximately three minutes. Since ROBAXIN Injectable is hypertonic, vascular extravasation must be avoided. A recumbent position will reduce the likelihood of side reactions.

Blood aspirated into the syringe does not mix with the hypertonic solution. This phenomenon occurs with many other intravenous preparations. The blood may be injected with the methocarbamol, or the injection may be stopped when the plunger reaches the blood, whichever the physician prefers.

The compositions of the present invention avoid or minimize the potential for extravasation and other issues caused by hypertonicity because the present invention compositions are isotonic. This is another significant safety improvement over the prior compositions. In one embodiment, an isotonic solution or composition can have an osmotic pressure of about 250-350 mOsmol/Kg. One of skill in the art is well aware of how to measure and adjust the tonicity of a solution. See for example, Remington: The Science and Practice of Pharmacy, Chapter 18, $21^{st}$ Edition, David B. Troy, Editor, Lippincott, Williams & Wikins 2006.

Accordingly, the present formulations include a tonicity agent. Any suitable tonicity agent can be used in the current formulations. In one aspect, the tonicity agent can be sodium chloride, dextrose, or their equivalents. One of skill in the art is aware of making compositions isotonic using a tonicity agent such as sodium chloride or dextrose or their equivalents. Examples of such equivalents include but not limited to mannitol, sorbitol, glycerin, and propylene glycol. See for example, Remington: The Science and Practice of Pharmacy, $19^{th}$ Ed., 1995, 613-27. Thus, in one aspect, the tonicity agent can be selected from the group consisting of sodium chloride, mannitol, sorbitol, dextrose, or organic solvents such as ethanol, glycerin, sorbitol, propylene glycol, etc., or a combination thereof The amount of tonicity agent in a given formulation can be selected on the nature of the tonicity agent and the tonicity of the composition without the tonicity agent. In one embodiment, the tonicity agent can be present in an amount sufficient to achieve an osmotic pressure of about 250-350 mOsmol/Kg in the formulation. In another embodiment, the tonicity agent can be present in an amount sufficient to achieve an osmotic pressure of about 275-325 mOsmol/Kg in the formulation. In another embodiment, the tonicity agent can be present in an amount sufficient to achieve an osmotic pressure of about 300 mOsmol/Kg in the formulation.

Thus, it has been surprisingly discovered that a ready-to-use, isotonic methocarbamol composition at a concentration of from about 1 mg/ml to about 10 mg/ml, or preferably 1 mg/ml to about 3 mg/ml, or preferably from about 3 mg/ml to about 5 mg/ml, in an aqueous vehicle provides a stable, isotonic, and particulate-free composition that reduces or prevents adverse health effects associated with administration of an injectable methocarbamol composition. Accordingly, the compositions and dosage forms of the present technology can reduce or avoid the potential for latex allergy and extravasation, and can permit administration of methocarbamol to subjects with renal pathology.

Therefore, the present invention provides compositions that are safer and easier to administer compared to the prior methocarbamol compositions at least for the following reasons: a) the compositions are administrable to subjects without undue concern over their renal pathology and thus demand less caregivers' attention; b) the compositions do not cause undue concern of extravasation because the compositions are isotonic; c) the compositions eliminate the possibility of latex sensitivity; and d) the compositions are ready-to-administer by intravenous infusion, thereby reducing contamination and dilution errors that may be caused by the necessity to dilute prior compositions.

Further, one of skill in the art recognizes that an ideal composition should have as few excipients as possible for an intravenous administration. In that sense, the present invention comprising predominantly or exclusively of water for injection or other suitable injectable grade water is highly recommended as the vehicle of choice. However, it is well within the scope of this invention to prepare and administer methocarbamol compositions that have a solubilizer. As used herein, the term "solubilizer" refers to pharmaceutically acceptable excipients that aid in the solubilization of methocarbamol in water. Non-limiting examples of suitable solubilizers include PEG, glycerin, propylene glycol, polysorbate 80, a dextran derivative such as betacyclodextrin, or its pharmaceutically acceptable derivatives, or a mixture of any of the foregoing, in sufficient quantity such that solubilities of greater than 10 mg/ml, or 20 mg/ml, or 30 mg/ml, or 40 mg/ml, or 50 mg/ml, or even higher can be obtained without being hypertonic. So long as such solubilizers are less than 56 wt % of the vehicle, such compositions are within the scope of this invention. Thus, in one aspect, the compositions of the present invention comprise a vehicle consisting essentially of water and a solubilizer of methocarbamol in amount of less than 56 wt %, wherein the methocarbamol is present at a concentration ranging from 2 mg/ml to about 50 mg/ml and the composition is isotonic, and is substantially free or free of latex sensitivity. In another aspect, the compositions of the present invention do not contain a solubilizer or are substantially free of a solubilizer.

In one embodiment, the pH of the compositions and dosage forms of the present invention may be unadjusted, in which case, it may be about 6.0. In other embodiments, the pH of the compositions and dosage forms of the present invention may be adjusted. When the pH is to be adjusted, any suitable pH adjuster can be used, optionally in combination with a suitable buffer. Non-limiting examples of pH adjusters can include sodium hydroxide, potassium hydroxide, hydrochloric acid, sulfuric acid, or organic pH adjusters such as cysteine, lysine, acetic acid, citric acid, and the like. If buffer is included in the composition, the choice of buffer may be influenced by the desired pH. In some examples, a suitable buffer for an organic pH adjuster may be its conjugate base (e.g., a citrate salt for citric acid, an acetate salt for acetic acid, etc.). Any appropriate concentration of acid or base may be used, such as from about 0.1M to about 1M or more. The pH of the compositions can be any suitable pH that does not produce unacceptable degradation. In one aspect, the pH can be from about 3 to about 9. In another aspect, the pH can be from about 4 to about 9. In another aspect, the pH can be from about 4 to about 8. In another aspect the pH can be from about 3 to about 5. In another aspect the pH can be from about 3.5 to about 5. In another aspect the pH can be from about 3.5 to about 4.5. In another aspect the pH can be from about 4 to about 5.5. In another aspect the pH can be from about 4 to about 5. In another aspect the pH can be from about 4 to about 4.5. In another aspect the pH can be from about 5.5 to about 8. In another aspect the pH can be from about 6 to about 7.5. In embodiments where the compositions, solutions, or dosage forms of the present invention are free of PEG, or substantially free of PEG, the pH is preferably from about 3 to about 5, about 3.5 to about 5, or about 4 to about 5. In specific examples where the compositions, solutions, or dosage forms of the present invention are free of PEG, or substantially free of PEG, the pH may be about 3.5 to about 4.5, or about 4 to about 4.5. To maintain the desired pH, PEG-free or substantially PEG-free compositions with a pH from about 3 to about 5 may contain a buffer. Non-limiting examples of suitable buffers include citrate, acetate, gluconate, lactate, tartarate, and the like.

The compositions and dosage forms of the current technology can also have any suitable viscosity for an injectable composition. In one aspect, the viscosity of the methocarbamol composition can be less than 50 centipoise (cps). Less than 50 cps can include all subranges less than 50 cps, such as less than 49, 45, 40, 37, 32, 30, 25, 20, 18, 15, 12, 10, and 5 cps. Methods of determining viscosity of pharmaceutical compositions are generally known in art. For example, USP XXXII, Chapter 911 describes suitable methods for determining the viscosity of a composition.

Methods of Administration

In one aspect, methocarbamol is administered by a caregiver such as a nurse, nurse practitioner, physician, physician assistant, or other healthcare personnel. The caregiver is provided with instructions by way of a patient guide, medication guide, drug product labeling, or verbal instructions that the methocarbamol ready-to-use compositions of the present invention may be administered to all subjects in need thereof regardless of their renal pathology status. For example, said subjects include those with normal renal function as well as those with reduced renal function. An example of reduced renal function is a creatinine clearance value of less than about 107 mL/min or less than about 1.8 mL/sec in men younger than 40 and less than about 87 mL/min or less than about 1.5 mL/sec in women younger than 40. Another example is a BUN to creatine ratio of greater than about 25. These are non-limiting examples of assessing and/or determining the renal status of a subject. Depending on the subject's age, sex, weight, and other physiological and/or disease states, these parameters could vary. However, one of skill in the art readily understands how to assess and determine the renal status of a subject.

To facilitate said administration, in one aspect, the ready to use methocarbamol drug product is supplied with written instructions that the composition of the present invention may be administered regardless of the status of renal pathology of the subject needing methocarbamol. In an alternative aspect, the instructions may specifically provide that said composition may be administered to subjects with renal pathology. In yet another aspect, the instructions may simply omit any reference to renal pathology or do not describe any contraindication to administering said compositions to subjects with renal pathology. Similarly, in one aspect, the written instructions simply omit any reference to latex allergy, and/or extravasation potential. Alternatively, the instructions describe a reduced risk of latex allergy and/or extravasation with current compositions as compared to prior art compositions.

In one aspect, the compositions of the present invention are provided to a subject in need thereof with a ready to use composition in a container that is amenable to deliver the ready to use composition as an intravenous infusion. As described above, the container can be provided in any suitable size, such as 50 ml, 100 ml, 125 ml, 150 ml, 200 ml, 250 ml, 400 ml, 500 ml, 750 ml, or 1000 ml or larger containers made of preferably a polymeric material such as polypropylene or polyethylene or a mixture thereof. Alternatively, said containers can be made of glass. Typically, the composition may be administered at a rate from about 1 to 20 ml/minute; 1-10 ml/minute; 1-5 ml/minute; 1-3 ml/minute; 1-2 ml/minute, or 1 ml/minute or even less than 1 ml/minute. These rates are followed for infusions that last between about 10 minutes to about 200 minutes. In some cases where a prolonged drip administration is desired, a slower rate of 0.5 ml/minute is used.

In one embodiment, a method for preventing an adverse health effect associated with administration of an injectable methocarbamol composition to a subject is described. The method can include administering a pre-mixed, injectable methocarbamol composition from a container to the subject a therapeutically effective amount of the pre-mixed methocarbamol composition. The methocarbamol composition can include methocarbamol in an amount from about 1 mg/ml to about 20 mg/ml, a tonicity agent, water, and less than 0.56 mg/ml PEG. The composition can be isotonic, stable, particulate-matter-free, and have a pH of from about 4 to about 9.

The therapeutically effective amount of the composition can provide any suitable amount of methocarbamol to the subject. In one aspect, the therapeutically effective amount can provide from about 1 gram (g) to about 6 g methocarbamol per day. In one aspect, the therapeutically effective amount can provide from about 3 g to about 5 g methocarbamol per day. In one aspect, the therapeutically effective amount can provide from about 4 g methocarbamol per day. The therapeutically effective amount can be administered over any suitable number of doses. In one example, the therapeutically effective amount is administered in multiple doses, such as 4 or more individual doses per day. In another example, the therapeutically effective amount is administered in 2 or more individual doses per day. In another example, the therapeutically effective amount is administered in 1 or more individual doses per day.

EXAMPLE EMBODIMENTS

The current technology can be further illustrated through a number of non-limiting example embodiments, as follows:

In one example, an injectable methocarbamol composition is described.

This composition can include methocarbamol in an amount from about 1 mg/ml to about 10 mg/ml, a tonicity agent, water; and less than 56 wt % polyethylene glycol (PEG), wherein the composition is isotonic.

In one example, the composition is sufficiently stable to allow at least 95 w/v % of the methocarbamol in the composition to remain undegraded and unprecipitated for at least 3 months at ambient temperature.

In one example, the composition is sufficiently stable to allow at least 95 wt % of the methocarbamol in the composition to remain undegraded and unprecipitated for at least 6 months.

In one example, the composition is sufficiently stable to allow at least 95 wt % of the methocarbamol in the composition to remain undegraded and unprecipitated for at least 1 year.

In one example, the composition is particulate-matter-free.

In one example, methocarbamol is present in an amount from 1 to 10 mg/ml.

In one example, methocarbamol is present in an amount from 3 to 7 mg/ml.

In one example, methocarbamol is present in an amount from about 5 to 10 mg/ml.

In one example, the composition has an osmotic pressure of about 250-350 mOsmol/Kg.

In one example, the tonicity agent is selected from the group consisting of sodium chloride, mannitol, sorbitol, dextrose, ethanol, glycerin, propylene glycol, and combinations thereof.

In one example, the PEG is selected from the group consisting of PEG-200, PEG-300, PEG-400, and combinations thereof.

In one example, the amount of PEG is less than 10 wt %.

In one example, the amount of PEG is less than 5 wt %.

In one example, the composition is substantially free of PEG.

In one example, the composition is free of PEG.

In one example, the composition further includes a pH adjuster and/or a buffer.

In one example, the composition has a pH of from about 4 to about 9.

In one example, the composition has a pH from about 4 to about 5.5.

In one example, the composition has a pH from about 4 to about 5.

In one example, the composition has a pH from about 4 to about 4.5.

In one example, the composition has a pH from about 5.5 to about 8.

In one example, the composition has a viscosity of less than 30 centipoise (cps).

In one example, an injectable methocarbamol dose or dosage form is described. The dose or dosage from can include methocarbamol in an amount from about 1 mg/ml to about 20 mg/ml, a tonicity agent, water; and less than 56 wt % polyethylene glycol (PEG), wherein the dosage form is isotonic.

In one example, the dose or dosage form is sufficiently stable to allow at least 95 w/v % of the methocarbamol in the composition to remain undegraded and unprecipitated for at least 3 months at ambient temperature.

In one example, the dose or dosage form is sufficiently stable to allow at least 95 wt % of the methocarbamol in the composition to remain undegraded and unprecipitated for at least 6 months.

In one example, the dose or dosage form is sufficiently stable to allow at least 95 wt % of the methocarbamol in the composition to remain undegraded and unprecipitated for at least 1 year.

In one example, the dose or dosage form is particulate-matter-free.

In one example, methocarbamol is present in an amount from 1 to 10 mg/ml.

In one example, methocarbamol is present in an amount from 3 to 7 mg/ml.

In one example, methocarbamol is present in an amount from 5 to 20 mg/ml.

In one example, the dose or dosage form has an osmotic pressure of about 250-350 mOsmol/Kg.

In one example, the tonicity agent is selected from the group consisting of sodium chloride, mannitol, sorbitol, dextrose, ethanol, glycerin, sorbitol, propylene glycol, and combinations thereof.

In one example, the PEG is selected from the group consisting of PEG-200, PEG-300, PEG-400, and combinations thereof.

In one example, the amount of PEG is less than 20 wt %.

In one example, the amount of PEG is less than 10 wt %.

In one example, the amount of PEG is less than 5 wt %.

In one example, the composition is substantially free of PEG.

In one example, the composition is free of PEG.

In one example, the dose or dosage form further includes a pH adjuster and/or a buffer.

In one example, the dose or dosage form has a pH of from about 4 to about 9.

In one example, the composition has a pH from about 4 to about 5.5.

In one example, the composition has a pH from about 4 to about 5.

In one example, the composition has a pH from about 4 to about 4.5.

In one example, the dose or dosage form has a pH from about 5.5 to about 8.

In one example, the dose or dosage form has a viscosity of less than 30 centipoise (cps).

In one example, a system for administration of an injectable methocarbamol composition is described. The system can include a container and a methocarbamol composition. The methocarbamol composition can include methocarbamol in an amount from 1 mg/ml to 10 mg/ml, a tonicity agent, water, and less than 50 v/v % PEG, wherein the container holds a volume of the composition from about 50 ml to about 1000 ml, and wherein the composition is isotonic.

In one example, the container is made of a material comprising polyethylene, polypropylene, or combinations thereof.

In one example, the container holds a volume of the composition from about 50 ml to about 500 ml.

In one example, a single container includes a single injectable dose of the composition.

In one example, a single container includes a plurality of injectable doses of the composition.

In one example, the composition has a pH from about 4 to about 9.

In one example, the composition has a pH from about 4 to about 5.5.

In one example, the composition has a pH from about 4 to about 5.

In one example, the composition has a pH from about 4 to about 4.5.

In one example, the composition is suitable for administration without further dilution.

In one example, the composition is particulate-matter-free.

In one example, the composition is terminally sterilized.

In one example, the composition is filter sterilized.

In one example, the composition has less than 20 v/v % PEG.

In one example, the composition has less than 10 v/v % PEG.

In one example, the composition has less than 5 v/v % PEG.

In one example, the composition is substantially free of PEG.

In one example, the composition is free of PEG.

In one example, the system further includes either instructions that instruct an administrator of the composition to administer to composition regardless of the renal pathology of the intended subject or instructions that omit a contraindication for patients having renal pathology.

In one example, a method of preventing an adverse health effect associated with administration of an injectable methocarbamol composition to a subject is described. The method can include removing a pre-mixed, injectable methocarbamol composition from a container and administering to the subject a therapeutically effective amount of the pre-mixed methocarbamol composition. The methocarbamol composition can include methocarbamol in an amount from 1 mg/ml to 10 mg/ml, a tonicity agent, water; and less than 56 w/v % PEG, wherein the composition is isotonic.

In one example, the composition is substantially free of PEG.

In one example, the composition is free of PEG.

In one example, the adverse health effect includes latex sensitivity, extravasation, a pathological renal event, or combinations thereof.

In one example, the composition is pre-mixed no less than 3 hours prior to administration.

In one example, the composition has a pH from about 3 to about 9.

In one example, the composition has a pH from about 3 to about 5.

In one example, the composition has a pH from about 3 to about 4.5.

In one example, the composition has a pH from about 3.5 to about 4.5.

In one example, the composition has a pH from about 4 to about 9.

In one example, the composition has a pH from about 4 to about 5.5.

In one example, the composition has a pH from about 4 to about 5.

In one example, the composition has a pH from about 4 to about 4.5.

In one example, the composition is stable.

In one example, the composition is particulate-matter-free.

In one example, the composition is a ready-to-administer composition.

In one example, the container is a latex-free container.

In one example, the therapeutically effective amount provides from about 1 g to about 6 g methocarbamol per day.

In one example, the therapeutically effective amount provides from about 3 g to about 5 g per day.

In one example, removing and administering occur contemporaneously.

In one example, removing occurs prior to administering.

In one example, an injectable methocarbamol composition is described.

This composition comprises or consists essentially of methocarbamol in an amount from about 1 mg/ml to less than 10 mg/ml, a tonicity agent, a pH adjuster, a buffer, and water, wherein the composition is isotonic and substantially free of PEG. The composition has a pH from about 4 to about 5.5, preferably from about 4 to about 5.0, more preferably from about 4 to about 4.5, even more preferably from about 4 to about 4.3. In certain embodiments, methocarbamol is present in an amount from 1 to 7 mg/ml, or from 3 to 7 mg/ml. In a specific embodiment, methocarbamol is present at about 5 mg/ml. The tonicity agent may be selected from the group consisting of sodium chloride, mannitol, sorbitol, dextrose, and combinations thereof. In a specific embodiment, the tonicity agent is sodium chloride. The osmotic pressure of the composition may be about 250-350 mOsmol/Kg. In some embodiments, the composition does not contain a solubilizer. In various embodiments, the composition is sufficiently stable to (a) allow at least 95 w/v % (e.g., 95 w/v %, 96 w/v %, 97 w/v %, 98 w/v %, 99 w/v %, or more) of the methocarbamol in the composition to remain undegraded and unprecipitated after storage for at least 3 months (e.g., 3, 6, 9, 12, 18, 24 months or more) at 25° C. and 60% relative humidity, and/or (b) result in an amount of the β-isomer that is about 1.0 w/w %, about 0.5% w/w or less, when measured by standard analytical techniques such as HPLC, UPLC, and the like, after storage for at least 3 months (e.g., 3, 6, 9, 12, 18, 24 months or more) at 25° C. and 60% relative humidity, and/or (c) result in an amount of guaifenesin that is about 1.0 w/w %, about 0.5% w/w or less, when measured by analytical techniques such as HPLC, UPLC, and the like, after storage for at least 3 months (e.g., 3, 6, 9, 12, 18, 24 months or more) at 25° C. and 60% relative humidity, and/or (d) result in a total amount of impurities that is about 1.0 w/w %, about 0.8% w/w or less, when measured by analytical techniques such as HPLC, UPLC, and the like, after storage for at least 3 months (e.g., 3, 6, 9, 12, 18, 24 months or more) at 25° C. and 60% relative humidity.

In one example, an injectable methocarbamol composition is described. This composition comprises or consists essentially of methocarbamol in an amount from about 1 mg/ml to less than 10 mg/ml, a tonicity agent, a pH adjuster, a buffer, and water, wherein the composition is isotonic and free of PEG. The composition has a pH from about 4 to about 5.5, preferably from about 4 to about 5.0, more preferably from about 4 to about 4.5, even more preferably from about 4 to about 4.3. In certain embodiments, methocarbamol is present in an amount from 1 to 7 mg/ml, or from 3 to 7 mg/ml. In a specific embodiment, methocarbamol is present at about 5 mg/ml. The tonicity agent may be selected from the group consisting of sodium chloride, mannitol, sorbitol, dextrose, and combinations thereof. In a specific embodiment, the tonicity agent is sodium chloride. The osmotic pressure of the composition may be about 250-350 mOsmol/Kg. In some embodiments, the composition does not contain a solubilizer. In various embodiments, the composition is sufficiently stable to (a) allow at least 95 w/v % (e.g., 95 w/v %, 96 w/v %, 97 w/v %, 98 w/v %, 99 w/v %, or more) of the methocarbamol in the composition to remain undegraded and unprecipitated after storage for at least 3 months (e.g., 3, 6, 9, 12, 18, 24 months or more) at 25° C. and 60% relative humidity, and/or (b) result in an amount of the β-isomer that is about 1.0 w/w %, about 0.5% w/w or less, when measured by analytical techniques such as HPLC, UPLC, and the like, after storage for at least 3 months (e.g., 3, 6, 9, 12, 18, 24 months or more) at 25° C. and 60% relative humidity, and/or (c) result in an amount of guaifenesin that is about 1.0 w/w %, about 0.5% w/w or less, when measured by analytical techniques such as HPLC, UPLC, and the like, after storage for at least 3 months (e.g., 3, 6, 9, 12, 18, 24 months or more) at 25° C. and 60% relative humidity, and/or (d) result in a total amount of impurities that is about 1.0 w/w %, about 0.8% w/w or less, when measured by analytical techniques such as HPLC, UPLC, and the like, after storage for at least 3 months (e.g., 3, 6, 9, 12, 18, 24 months or more) at 25° C. and 60% relative humidity.

Of course, it is to be understood that the above-described arrangements are only illustrative of the application of the principles of the present invention. Numerous modifications and alternative arrangements may be devised by those skilled in the art without departing from the spirit and scope of the present invention and the appended claims are intended to cover such modifications and arrangements. Thus, while the present invention has been described above with particularity and detail in connection with what is presently deemed to be the most practical and preferred embodiments of the invention, it will be apparent to those of ordinary skill in the art that numerous modifications, including, but not limited to, variations in size, materials, shape, form, function and manner of operation, assembly and use may be made without departing from the principles and concepts set forth herein.

Numbered Exemplary Embodiments Embodiment 1: An injectable methocarbamol solution comprising: methocarbamol in an amount from about 1 mg/ml to less than 10 mg/ml; a tonicity agent; a buffer; and water; wherein the solution is isotonic, has a pH of about 3 to about 5, and is free of polyethylene glycol (PEG).

Embodiment 2: The solution of embodiment 1, wherein the solution is sufficiently stable to allow at least 95 w/v % of the methocarbamol in the composition to remain undegraded and unprecipitated after storage for at least 3 months at 25° C. and 60% relative humidity.

Embodiment 3: The solution of embodiment 1, wherein the solution is sufficiently stable to allow at least 95 wt % of the methocarbamol in the composition to remain undegraded and unprecipitated after storage for at least 6 months at 25° C. and 60% relative humidity.

Embodiment 4: The solution of embodiment 1, wherein the solution is sufficiently stable to allow at least 95 wt % of the methocarbamol in the composition to remain undegraded and unprecipitated after storage for at least 1 year at 25° C. and 60% relative humidity.

Embodiment 5: The solution of embodiment 1, wherein the solution is particulate-matter-free.

Embodiment 6: The solution of embodiment 1, wherein methocarbamol is present in an amount from about 1 mg/ml to about 7 mg/ml.

Embodiment 7: The solution of embodiment 1, wherein methocarbamol is present in an amount from about 3 mg/ml to about 7 mg/ml.

Embodiment 8: The solution of embodiment 1, wherein the solution has an osmotic pressure of about 250-350 mOsmol/Kg.

Embodiment 9: The solution of embodiment 1, wherein the tonicity agent is selected from the group consisting of sodium chloride, mannitol, sorbitol, dextrose, ethanol, glycerin, propylene glycol, and combinations thereof.

Embodiment 10: The solution of embodiment 1, further comprising a pH adjusting agent.

Embodiment 11: The solution of embodiment 1, wherein the solution has a pH of from about 3.5 to about 4.5.

Embodiment 12: The solution of embodiment 1, wherein the solution has a pH of about 4.0 to about 4.5.

Embodiment 13: The solution of embodiment 1, wherein the solution has about 1.0% w/w or less of 1-hydroxy-3-(2-methoxyphenoxy)propan-2-yl carbamate after storage for at least 3 months at 25° C. and 60% relative humidity.

Embodiment 14: The solution of embodiment 13, wherein the solution has about 0.5% w/w or less of 1-hydroxy-3-(2-methoxyphenoxy)propan-2-yl carbamate after storage for at least 3 months at 25° C. and 60% relative humidity.

Embodiment 15: The solution of embodiment 1, wherein the solution has about 1.0% w/w or less of 1-hydroxy-3-(2-methoxyphenoxy)propan-2-yl carbamate after storage for at least 6 months at 25° C. and 60% relative humidity.

Embodiment 16: The solution of embodiment 15, wherein the solution has about 0.5% w/w or less of 1-hydroxy-3-(2-methoxyphenoxy)propan-2-yl carbamate after storage for at least 6 months at 25° C. and 60% relative humidity.

Embodiment 17: The solution of embodiment 1, wherein the solution has about 1.0% w/w or less of 1-hydroxy-3-(2-methoxyphenoxy)propan-2-yl carbamate after storage for at least 12 months at 25° C. and 60% relative humidity.

Embodiment 18: The solution of embodiment 1, wherein the solution has about 0.5% w/w or less of 1-hydroxy-3-(2-methoxyphenoxy)propan-2-yl carbamate after storage for at least 12 months at 25° C. and 60% relative humidity.

Embodiment 19: The solution of embodiment 1, wherein the solution has about 1.0% w/w or less of 1-hydroxy-3-(2-methoxyphenoxy)propan-2-yl carbamate after storage for at least 24 months at 25° C. and 60% relative humidity.

Embodiment 20: The solution of embodiment 1, wherein the dosage form has about 0.5% w/w or less of 1-hydroxy-3-(2-methoxyphenoxy)propan-2-yl carbamate after storage for at least 24 months at 25° C. and 60% relative humidity.

Embodiment 21: An injectable methocarbamol solution, comprising: methocarbamol in an amount from about 1 mg/ml to less than 10 mg/ml; a tonicity agent; a buffer; and water; wherein the solution is isotonic, has a pH of about 3 to about 5, is free of polyethylene glycol (PEG), and has about 1.0% w/w or less of 1-hydroxy-3-(2-methoxyphenoxy)propan-2-yl carbamate after storage for at least 12 months at 25° C. and 60% relative humidity.

Embodiment 22: A method of minimizing an adverse health effect associated with methocarbamol administration to a subject, comprising: administering a therapeutically effective amount of methocarbamol to the subject in a dosage form as recited in embodiment 1.

Embodiment 23: The method of embodiment 22, wherein the adverse health effect includes latex sensitivity, extravasation, a pathological renal event, or combinations thereof.

Embodiment 24: The method of embodiment 23, wherein the adverse heath effect is a pathological renal event.

Embodiment 25: The method of embodiment 22, wherein the dosage form is a ready-to-use composition that can be administered without further dilution.

Embodiment 26: The method of embodiment 22, wherein the therapeutically effective amount provides from about 1 g to about 6 g methocarbamol per day.

Embodiment 27: The method of embodiment 22, wherein the therapeutically effective amount provides from about 3 g to about 5 g per day.

Embodiment 28: The method of embodiment 22, wherein the therapeutically effective amount is sufficient to induce muscle relaxation.

Embodiment 29: A process for preparing a solution of methocarbamol, the process comprising: acidifying water to a pH of about 3 to about 5, wherein the acidifying comprises adding a pH adjusting agent to the water; and contacting the acidified water with methocarbamol to form a solution of methocarbamol, wherein the solution has about 1.0 w/w % or less of 1-hydroxy-3-(2-methoxyphenoxy)propan-2-yl carbamate.

Embodiment 30: The process of embodiment 29, wherein the pH of the acidified water is about pH 3.5 to about pH 4.5.

Embodiment 31: The process of embodiment 29, wherein the pH of the acidified water is about pH 4 to about pH 5.

Embodiment 32: The process of embodiment 29, wherein the pH of the acidified water is about pH 4 to about pH 4.5

Embodiment 33: The process of embodiment 29, wherein the process further comprises adding a buffer prior to adding the pH adjusting agent.

Embodiment 34: The process of embodiment 33, wherein the pH adjusting agent is an organic acid and the buffer is a conjugate base of the organic acid.

Embodiment 35: The process of embodiment 34, wherein the pH adjusting agent is citric acid or acetic acid.

Embodiment 36: The process of embodiment 35, wherein the pH adjusting agent is citric acid and the buffer is sodium citrate.

Embodiment 37: The process of embodiment 35, wherein the pH adjusting agent is acetic acid and the buffer is sodium acetate.

Embodiment 38: The process of embodiment 29, wherein the contacting comprises adding about 1 mg to about 10 mg of methocarbamol per mL of acidified water.

Embodiment 39: The process of embodiment 29, wherein the contacting comprises adding about 1 mg to no more than 10 mg of methocarbamol per mL of acidified water.

Embodiment 40: The process of embodiment 29, wherein the contacting comprises adding about 1 mg to less than 10 mg of methocarbamol per mL of acidified water.

Embodiment 41: The process of embodiment 29, wherein the contacting comprises adding about 1 mg to about 7 mg of methocarbamol per mL of acidified water.

Embodiment 42: The process of embodiment 29, wherein the solution has about 0.5 w/w % or less of 1-hydroxy-3-(2-methoxyphenoxy)propan-2-yl carbamate.

Embodiment 43: The process of embodiment 29, wherein the solution has about 0.3 w/w % or less of 1-hydroxy-3-(2-methoxyphenoxy)propan-2-yl carbamate.

Embodiment 44: The process of embodiment 29, wherein the solution has about 0.1 w/w % or less of 1-hydroxy-3-(2-methoxyphenoxy)propan-2-yl carbamate.

Embodiment 45: The process of embodiment 29, wherein the solution is substantially free of 1-hydroxy-3-(2-methoxyphenoxy)propan-2-yl carbamate.

Embodiment 46: The process of embodiment 29, wherein the solution is free of PEG or is substantially free of PEG.

Embodiment 47: The process of embodiment 29, wherein the process further comprises adding a tonicity agent to the water prior to the addition of the pH adjusting agent.

Embodiment 48: The process of embodiment 47, wherein the tonicity agent is sodium chloride.

Embodiment 49: The process of embodiment 29, wherein the acidifying and contacting are performed at ambient temperature.

Embodiment 50: The process of embodiment 29, wherein the acidifying and contacting are performed at about 30° C. to about 60° C.

Embodiment 51: The process of embodiment 50, wherein the acidifying and contacting are performed at about 50° C.

Embodiment 52: The process of embodiment 29, further comprising filling a container with the solution and sealing.

Embodiment 53: The process of embodiment 52, wherein the container is a silica-lined glass vial or a polypropylene bag.

Embodiment 54: The process of embodiment 29, further comprising filter sterilizing the solution, and then aseptically filling a container with the sterile solution and sealing.

Embodiment 55: The process of embodiment 54, wherein the container is a vial or a pharmaceutically acceptable infusion bag.

Embodiment 56: A method of administering methocarbamol solution for infusion, the method comprising administering a 5 mg/mL methocarbamol solution at a rate of infusion ranging from about 5 mg/minute to about 100 mg/minute, from a pharmaceutically acceptable sterile container that has a volume of about 50 mL to about 1000 mL, wherein the 5 mg/mL methocarbamol solution for injection is free of polyethylene glycol, is buffered in the pH range of about 3 to about 5, and contains less than 1.0% w/w of 1-hydroxy-3-(2-methoxyphenoxy)propan-2-yl carbamate and less than 1.0% w/w of guaifenesin.

Process for Preparing a Methocarbamol Composition

As will be apparent to one skilled in the art after reviewing the present disclosure, there can be numerous ways to prepare methocarbamol compositions of the present disclosure, including a ready-to-use formulation according to the current technology.

In one specific example, a methoocarbamol composition can be prepared in the following general manner. Methocarbamol is weighed and dissolved in warm water for injection. If buffer is included in the formulation, it can be added and dissolved in water for injection prior to the addition of methocarbomol. To the solution, the required quantity of tonicity agent is added and dissolved. If required, the pH of the solution is adjusted with an appropriate pH adjuster, such as HCl or NaOH. If desired, a solubilizer such as propylene glycol, a dextran or the like can be added. The final volume of the solution is made with water for injection. The solution is then filtered, filled into type I glass vials or flexible polypropylene containers and steam sterilized in an autoclave at about 121 degrees C. for about 15-30 minutes. A suitable alternative to polypropylene bag container can be a polyvinylchloride or a polyethylene/polyolefin or a combination thereof. Additionally, the product may be sterilized aseptically.

In another specific example, a methocarbamol composition can be prepared as generally described above, but with the order-of-addition of ingredients altered. Specifically, all excipients (e.g., tonicity agent, buffer, pH adjuster, etc.) are measured out and dissolved in warm Water for Injection prior to the addition of methocarbamol. In one example, the required amount of the tonicity agent is weighed and dissolved in warm Water for Injection (e.g., about 45-55° C.). If buffer is included in the formulation, it is added and dissolved in the solution prior to adjustment of the pH of the solution with an appropriate pH adjuster (e.g., citric acid if the buffer was sodium citrate, etc.). The final volume of the solution is made with Water for Injection. The solution is then filtered (i.e., filter sterilized) and aseptically filled into an appropriate container (e.g., type I glass vials, flexible polypropylene containers, etc.). In another example, buffer is dissolved in warm Water for Injection prior to the addition of the tonicity agent. The above-described method is particularly preferred for embodiments free of PEG, or substantially free of PEG.

In yet another example, a methocarbamol composition can be prepared as described in either example above with the process further comprising controlling the pH during the process, such that the pH is less than about pH 5.9. Controlling the pH during the process is one strategy to reduce the amount of the β-isomer in a methocarbamol solution. In various embodiments, the pH may be less than about pH 5.8, less than about pH 5.7, less than about pH 5.6, less than about pH 5.5, less than about pH 5.4, less than about pH 5.3, less than about pH 5.2, less than about pH 5.1. In a specific embodiment, the pH during the process may be about pH 5.0 or less. In another specific embodiment, the pH during the process may be about pH 4.5 or less. The pH may be controlled by the use of one or more buffer and/or a pH adjusting agent. Suitable buffers and pH adjusting agents are described above.

EXAMPLES

The following several non-limiting examples further illustrate various iterations of the invention.

TABLE 1

Composition of Formulations 1-4

| Ingredients | Formulation 1 | Formulation 2 | Formulation 3 | Formulation 4 |
|---|---|---|---|---|
| Methocarbamol | 10 mg/ml | 10 mg/ml | 5 mg/ml | 15 mg/ml |
| Sodium chloride | 7.5 mg/ml | 7.5 mg/ml | 8 mg/ml | — |
| Propylene glycol | — | — | — | 20 mg/ml |
| HCl to adjust pH to | 4.0 | 6.4 (not adjusted) | 5.5 | 5.5 |
| Water for Injection | q.s. | q.s. | q.s. | q.s. |

TABLE 2

Composition of Formulations 5-8

| Ingredients | Formulation 5 | Formulation 6 | Formulation 7 | Formulation 8 |
|---|---|---|---|---|
| Methocarbamol | 10 mg/ml | 10 mg/ml | 10 mg/ml | 10 mg/ml |
| Dextrose | 37.5 mg/ml | — | — | — |
| Propylene glycol | — | — | 18.8 mg/ml | — |
| Mannitol | — | 37.5 mg/ml | — | — |
| Sorbitol solution (70%) | — | — | — | 70 mg/ml |
| Unadjusted pH | 6.4 | 6.1 | 6.4 | 6.3 |
| Water for Injection | q.s. | q.s. | q.s. | q.s. |

TABLE 3

Composition of Formulations 9-12

| Ingredients | Formulation 9 | Formulation 10 | Formulation 11 | Formulation 12 |
|---|---|---|---|---|
| Methocarbamol | 10 mg/ml | 10 mg/ml | 10 mg/ml | 10 mg/ml |
| Sodium chloride | 6.5 mg/ml | 6.5 mg/ml | 6.0 mg/ml | 7.5 mg/m1 |
| Sodium citrate | 1.5 mg/ml | 0.5 mg/ml | 1.0 mg/ml | |
| Sodium acetate | | | | 1.0 mg/ml |
| Citric acid/acetic acid/NaOH to adjust pH to | 5.5 | 5.5 | 5.5 | 5.5 |
| Water for Injection | q.s. | q.s. | q.s. | q.s. |

TABLE 4

Composition of Formulations 13-15

| Ingredients | Formulation 13 | Formulation 14 | Formulation 15 |
|---|---|---|---|
| Methocarbamol | 5 mg/ml | 5 mg/ml | 5 mg/ml |
| Sodium chloride | 7.5 mg/ml | 8.0 mg/ml | 8.5 mg/ml |
| Sodium citrate, dihydrate | 1 mg/ml | 1 mg/ml | 1 mg/ml |
| Citric acid, monohydrate adjust pH to | 4.0 | 4.0 | 4.0 |
| Water for Injection | q.s. | q.s. | q.s. |

TABLE 5

Composition of Formulations 16-18

| Ingredients | Formulation 16 | Formulation 17 | Formulation 18 |
|---|---|---|---|
| Methocarbamol | 5 mg/ml | 5 mg/ml | 5 mg/ml |
| Sodium chloride | 7.5 mg/ml | 8.0 mg/ml | 8.5 mg/ml |
| Sodium acetate | 1 mg/ml | 1 mg/ml | 1 mg/ml |
| Acetic acid adjust pH to | 4.0 | 4.0 | 4.0 |
| Water for Injection | q.s. | q.s. | q.s. |

Example 19

A 5 mg/mL methocarbamol formulation containing 0.9% sodium chloride, as per the composition in Table A below, was made at laboratory scale and subjected to a freeze-thaw study.

TABLE A

| | Formulation 19 | |
|---|---|---|
| Ingredient | mg/mL | Quantity/batch |
| Methocarbamol | 5.0 | 5004.1 mg |
| Sodium chloride | 9.0 | 9004.1 mg |
| pH (unadjusted) | — | 5.98 |
| Water for Injection | q.s. to 1 mL | q.s. to 1,000 mL |

Into a 1 L beaker, approximately 900 mL water was added and warmed to 54° C. 5 g methocarbamol was added and mixed. Methocarbamol dissolved in about 5 minutes. Temperature of the solution after dissolution of methocarbamol was 51° C. The beaker was kept in a cold water batch and cooled the solution to room temperature. 9 g of sodium chloride was added and mixed to dissolve. pH of the solution was measured to be 5.98. The volume was made up to 1000 mL in a volumetric flask and filtered. 100 mL aliquots of both the formulations were made in 100 mL clear vials.

One vial each was placed at −20° C. and 4° C. The rest of the vials were placed at RT. The −20° C. sample was subjected to three (3) freeze thaw cycles and tested for USP particulate matter. USP particulate results are given in Table B. 4° C. and RT samples were visually inspected for any particulates/precipitate. Crystallization/particulate matter was not observed.

TABLE B

| 10μ particles/100 mL | 173 |
|---|---|
| 25μ particles/100 mL | 20 |

Based on the positive results from the freeze/thaw studies, three (3) cGMP batches of Formulation 19, each 100 L, were made to evaluate the stability of the product for registration. However, pH increases and unacceptable levels of β-isomer impurity were observed after storage for 3 months at 40° C. and 75% RH (accelerated conditions, not shown) and at 25° C. and 60% RH (long term conditions, Table C).

TABLE C

| | | | Date Placed on Stability | After 3 Months Storage | |
|---|---|---|---|---|---|
| Test | Methods | Specifications | | Upright | Inverted |
| Physical Appearance A: Solution Description | USP <1> | A. Clear, colorless solution B. Essentially free of visible | A: Conforms B: Conforms | A: Conforms B: Conforms | A: Conforms B: Conforms |

TABLE C-continued

| Test | Methods | Specifications | Date Placed on Stability | After 3 Months Storage Upright | After 3 Months Storage Inverted |
|---|---|---|---|---|---|
| B: Visible Particulate Matter | | particulate matter | | | |
| Assay | Per USP | 90.0-110.0% Label Claim | 99.5% | 98.5% | 98.9% |
| pH | USP <791> | 4.5-6.5 | 5.2 | 5.1 | 5.1 |
| Impurities A. Guaifenesin B. β-isomer C. Indiv. Unspecified D. Total Impurities | HPLC | A. NMT 2.0% B. NMT 1.0% C. NMT 0.3% D. NMT 3.0% | A. 0.1% B. 0.8% C. ND D. 0.9% | A. 0.1% B. 1.1% C. ND D. 1.2% | A. 0.1% B. 1.2% C. ND D. 1.3% |
| Particulate Matter, per Container A. ≥10 μm A. ≥25 μm | USP <788> | A. NMT 6,000 B. NMT 600 | A. 218 B. 4 | A. 609 B. 2 | A. 387 B. 13 |
| Osmolality | USP <785> | 250-350 mOsm/kg | 309 mOsm/kg | 307 mOsm/kg | 308 mOsm/kg |

USP - United States Pharmacopeia, NMT- Not More Than, ND - Not Detected

Examples 20-21

A 5 mg/mL methocarbamol formulation, pH 4.0, containing 0.9% sodium chloride and a buffer, and as per the composition in Table D below, was made at laboratory scale and evaluated.

TABLE D

| | Formulation 20 | | Formulation 21 | |
|---|---|---|---|---|
| Ingredient | mg/mL | Quantity/batch | mg/mL | Quantity/batch |
| Methocarbamol | 5.0 | 5010.0 mg | 5.0 | 5012.0 mg |
| Sodium chloride | 9.0 | 9011.3 mg | 9.0 | 9004.9 mg |
| Sodium citrate dehydrate | 1.0 | 1004.8 mg | Nil | — |
| Sodium acetate, anhydrous | Nil | — | 1.0 | 1008.1 mg |
| Citric acid | q.s. to pH 4.0 | q.s. to pH 4.0 | Nil | |
| Acedc acid | Nil | — | q.s. to pH 4.0 | q.s. to pH 4.0 |
| Water for Injection | q.s. to 1 mL | q.s. to 1,000 mL | q.s. to 1 mL | q.s. to 1,000 mL |

Into a 1 L beaker, approximately 900 mL water was added. 9 g of sodium chloride was added and mixed to dissolve. 5 g methocarbamol was added and mixed. This mixture was warmed up to 40° C. by placing the beaker in a warm water bath and continued the mixing. Once the methocarbamol was completely dissolved, the formulation was cooled to room temperature by placing the beaker in a cooled water bath. 1000 mg of sodium citrate/acetate was added and mixed to dissolve. The pH was measured and adjusted to 4.0 using 10% citric acid solution or 10% acetic acid solution. The volume was made up to 1000 mL in a volumetric flask and filtered. 100 mL aliquots of both the formulations were made in 100 mL clear vials.

Three vials each from the above two formulations were stored at 40° C. and 75% RH for stability study. The remaining seven vials were stored at room temperature (25° C. and 60% RH). Samples were tested for pH (after 2 months) and chromatographic purity (after 3 months). The pH of the formulations was quite stable with the addition of 1.0 mg/mL Sodium citrate dihydrate or Sodium acetate buffer (Table E). The impurity profile was also improved (Table F). Impurities were measured as in Example 19.

TABLE E

| Sample/condition | Initial pH | pH after 1M | pH @ 2 M |
|---|---|---|---|
| Formulation 20 @ RT | 4.0 | 4.01 | 4.03 |
| Formulation 20 @ 40° C. | 4.0 | 4.00 | 4.03 |
| Formulation 21 @ RT | 4.0 | 4.00 | 4.01 |
| Formulation 21 @ 40° C. | 4.0 | 3.99 | 4.01 |

TABLE F

| Sample/condition | β-isomer | Guaifenesin | RRT 1.25 | Total impurities | Methocarbamol |
|---|---|---|---|---|---|
| Formulation 20 @ RT | 0 | 0.1% | 0 | 0.4% | 99.6% |
| Formulation 20 @ 40° C. | 0.3% | 0.1% | 0.1% | 1.1% | 98.9% |
| Formulation 21 @ RT | 0 | 0.1% | 0 | 0.7% | 99.3% |
| Formulation 21 @ 40° C. | 0.2% | 0.3% | 0.2% | 1.6% | 98.4% |

Examples 22-23

Formulations containing different concentrations of buffer (e.g., 0.25 mg/mL, 0.50 mg/mL or 1.0 mg/mL citrate buffer), but otherwise similar to Formulation 20, were next made and subjected to a heat stability study. All three formulations showed good stability after being subjected to elevated temperature (121° C. for 30 minutes, Table G).

TABLE G

| Methocarbamol formulation | Initial pH | End pH |
|---|---|---|
| Formulation 20 (Buffer: 1.0 mg/mL) | 4.00 | 4.04 |
| Formulation 22 (Buffer: 0.25 mg/mL) | 4.01 | 4.08 |
| Formulation 23 (Buffer: 0.5 mg/mL) | 4.00 | 4.06 |

Example 24

While formulations 19-21 were made at laboratory scale, in this example, three batches of Methocarbamol Injection 5 mg/mL, pH 4.0, containing 0.9% sodium chloride and a buffering agent were made to evaluate the stability of the product when manufactured at commercial scale (Table H). The manufacturing process was as described in Example 20.

TABLE H

| Composition | Per mL | Batch #1 | Batch #2 | Batch #3 |
|---|---|---|---|---|
| Methocarbamol, USP | 10.0 mg | 504.04 g[1] | 504.05 g[1] | 504.06 g[1] |
| Sodium chloride, USP | 8 mg | 800.01 g[2] | 800.01 g[2] | 800.01 g[2] |
| Sodium citrate dehydrate, USP | 1 mg | 100.00 g[2] | 100.04 g[2] | 100.03 g[2] |
| Citric acid monohydrate, USP | q.s. to pH 4.0 | q.s. to pH 4.0 | q.s. to pH 4.0 | q.s. to pH 4.0 |
| Water for Injection | q.s. to 1.0 mL | q.s. to 100 L | q.s. to 100L | q.s. to 100L |

[1]This value has been corrected for assay and water content.
[2]Actual quantity used.

Surprisingly, the β-isomer impurity at release, as measured by HPLC, was above 1% in all the three batches. Additional experimentation was undertaken to identify the source of the impurity. During the evaluation it was experimentally determined that the β-isomer impurity was being generated during the compounding process due to the addition of the methocarbamol prior to the addition of the buffer. Hence, a modified compounding procedure was developed to reduce the β-isomer impurity in product. In the modified compounding procedure, methocarbamol was added to a buffered solution after pH adjustment instead of being added to a buffered solution. This reduced the β-isomer impurity at the release as well as during the stability studies. Thus, the order of addition was critical.

Three additional batches (batches 4-6, Table I) were manufactured at commercial scale using the modified compounding procedure and dispensed into 100 mL USP type I clear molded glass vials. Stability of all three batches was evaluated under accelerated storage conditions (40 C, 75% RH) at 3 and 6 months (M), and under long term storage conditions (25 C, 60% RH) at 3, 6, 9, 12, 18, and 24 months (M). All samples conformed to appearance testing requirements (clear, colorless solution that is essentially free of visible particulate matter). pH and osmolality was also stable. Additional stability data for Batch #4 is shown in Table J. Stability data for the other two batches were similar.

TABLE I

| Composition | Function | Per mL | Batch #4 | Batch #5 | Batch #6 |
|---|---|---|---|---|---|
| Methocarbamol, USP | Active | 10.0 mg | 504.06 g[1] | 504.05 g[1] | 504.05 g[1] |
| Na chloride, USP | Tonicity Agent | 8 mg | 800.03 g[2] | 800.01 g[2] | 800.01 g[2] |
| Na citrate dehydrate, USP | Buffer | 1 mg | 100.03 g[2] | 100.03 g[2] | 100.03 g[2] |
| Citric acid monohydrate, USP | pH adjuster | q.s. to pH 4.0 | q.s. to pH 4.0 | q.s. to pH 4.0 | q.s. to pH 4.0 |
| Water for Injection | Vehicle | q.s. to 1.0 mL | q.s. to 100 L | q.s. to 100 L | q.s. to 100 L |

Na = sodium; USP = United States Pharmacopeia
[1]This value has been corrected for assay and water content.
[2]Actual quantity used

TABLE J

| Storage condition | pH | Assay | β-isomer | Guaifenesin | Unknown impurity | Total impurities |
|---|---|---|---|---|---|---|
| Initial | 4.0 | 100.7% | <QL | 0.1% | ND | 0.1% |
| 3M@40° C. | 4.0 | 100.3% | 0.3% | 0.2% | 0.08% | 0.5% |
| 6M@40° C. | 4.1 | 100.0% | 0.6% | 0.3% | 0.11% | 1.0% |
| 3M@25° C. | 4.0 | 100.6% | 0.1% | 0.1% | <QL | 0.2% |
| 6M@25° C. | 4.0 | 100.8% | 0.1% | 0.1% | <QL | 0.2% |
| 9M@25° C. | 4.1 | 101.2% | 0.1% | 0.1% | <QL | 0.2% |
| 12M@25° C. | 4.1 | 101.3% | 0.2% | 0.1% | <QL | 0.3% |
| 18M@25° C. | 4.1 | 101.2% | 0.2% | 0.2% | <QL | 0.4% |
| 24M@25° C. | 4.1 | 101.3% | 0.3% | 0.2% | 0.06% | 0.6% |

All tests were performed as described in Example 19.

What is claimed is:

1. An injectable methocarbamol solution for intravenous administration comprising:
   methocarbamol in an amount from about 1 mg/ml to less than 10 mg/ml;
   a tonicity agent; wherein the tonicity agent is selected from the group consisting of sodium chloride, mannitol, sorbitol, dextrose, ethanol, glycerin, sorbitol, propylene glycol, and combinations thereof;
   a buffer; and
   water,
   wherein the solution is isotonic, has a pH of about 3 to about 5, is free of polyethylene glycol (PEG), and contains no more than 2.0% w/w of guaifenesin after storage at ambient temperature for at least 3 months.

2. The solution of claim 1, wherein the solution is sufficiently stable to allow at least 95 w/v % of the methocarbamol in the composition to remain undegraded and unprecipitated after storage for at least 3 months at 25° C. and 60% relative humidity.

3. The solution of claim 1, wherein the solution is sufficiently stable to allow at least 95 wt % of the methocarbamol in the composition to remain undegraded and unprecipitated after storage for at least 6 months at 25° C. and 60% relative humidity.

4. The solution of claim 1, wherein the solution is sufficiently stable to allow at least 95 wt % of the methocarbamol in the composition to remain undegraded and unprecipitated after storage for at least 1 year at 25° C. and 60% relative humidity.

5. The solution of claim 1, wherein the solution is particulate-matter-free.

6. The solution of claim 1, wherein methocarbamol is present in an amount from about 1 mg/ml to about 7 mg/ml.

7. The solution of claim 1, wherein methocarbamol is present in an amount from about 3 mg/ml to about 7 mg/ml.

8. The solution of claim 1, wherein the solution has an osmotic pressure of about 250-350 mOsmol/Kg.

9. The solution of claim 1, wherein the solution has a pH of from about 3.5 to about 4.5.

10. The solution of claim 1, wherein the solution has a pH of about 4.0 to about 4.5.

11. The solution of claim 1, wherein the solution has about 1.0% w/w or less of 1-hydroxy-3-(2-methoxyphenoxy)propan-2-yl carbamate after storage for at least 3 months at 25° C. and 60% relative humidity.

12. The solution of claim 11, wherein the solution has about 0.5% w/w or less of 1-hydroxy-3-(2-methoxyphenoxy)propan-2-yl carbamate after storage for at least 3 months at 25° C. and 60% relative humidity.

13. The solution of claim 1, wherein the solution has about 1.0% w/w or less of 1-hydroxy-3-(2-methoxyphenoxy)propan-2-yl carbamate after storage for at least 6 months at 25° C. and 60% relative humidity.

14. The solution of claim 13, wherein the solution has about 0.5% w/w or less of 1-hydroxy-3-(2-methoxyphenoxy)propan-2-yl carbamate after storage for at least 6 months at 25° C. and 60% relative humidity.

15. The solution of claim 1, wherein the solution has about 1.0% w/w or less of 1-hydroxy-3-(2-methoxyphenoxy)propan-2-yl carbamate after storage for at least 12 months at 25° C. and 60% relative humidity.

16. The solution of claim 15, wherein the solution has about 0.5% w/w or less of 1-hydroxy-3-(2-methoxyphenoxy)propan-2-yl carbamate after storage for at least 12 months at 25° C. and 60% relative humidity.

17. The solution of claim 1, wherein the solution has about 1.0% w/w or less of 1-hydroxy-3-(2-methoxyphenoxy)propan-2-yl carbamate after storage for at least 24 months at 25° C. and 60% relative humidity.

18. The solution of claim 17, wherein the dosage form has about 0.5% w/w or less of 1-hydroxy-3-(2-methoxyphenoxy)propan-2-yl carbamate after storage for at least 24 months at 25° C. and 60% relative humidity.

19. A method of minimizing an adverse health effect associated with methocarbamol administration to a subject, comprising: intravenously administering a therapeutically effective amount of methocarbamol to the subject in a solution as recited in claim 1.

20. An injectable methocarbamol solution for intravenous administration comprising:
   methocarbamol in an amount from about 1 mg/ml to less than 10 mg/ml;
   a tonicity agent, wherein the tonicity agent is selected from the group consisting of sodium chloride, mannitol, sorbitol, dextrose, ethanol, glycerin, propylene glycol, and combinations thereof;
   a buffer selected from (I) sodium citrate and citric acid or (II) sodium acetate and acetic acid; and
   water,
   wherein the solution is isotonic, has a pH of about 3 to about 5, is free of polyethylene glycol (PEG), and contains no more than 2.0% w/w of guaifenesin after storage at ambient temperature for at least 3 months.

* * * * *